(12) United States Patent
Derkvist

(10) Patent No.: US 11,484,399 B2
(45) Date of Patent: Nov. 1, 2022

(54) STENT GRAFT WITH POCKETS

(71) Applicant: JOTEC GmbH, Hechingen (DE)

(72) Inventor: Stefan Derkvist, Hechingen (DE)

(73) Assignee: JOTEC GmbH, Hechingen (DE)

(*) Notice: Subject to any disclaimer, the term of this patent is extended or adjusted under 35 U.S.C. 154(b) by 0 days.

(21) Appl. No.: 16/693,850

(22) Filed: Nov. 25, 2019

(65) Prior Publication Data

US 2020/0085561 A1 Mar. 19, 2020

Related U.S. Application Data

(63) Continuation of application No. PCT/EP2018/065233, filed on May 30, 2018.

(30) Foreign Application Priority Data

May 31, 2017 (DE) .................. 10 2017 111 964.7

(51) Int. Cl.
*A61F 2/07* (2013.01)
*A61F 2/848* (2013.01)
(Continued)

(52) U.S. Cl.
CPC .............. *A61F 2/07* (2013.01); *A61F 2/848* (2013.01); *A61F 2/90* (2013.01);
(Continued)

(58) Field of Classification Search
CPC .... A61F 2/07; A61F 2/848; A61F 2/90; A61F 2002/075; A61F 2002/077;
(Continued)

(56) References Cited

U.S. PATENT DOCUMENTS 5,123,917 A   6/1992  Lee
5,843,166 A  12/1998  Lentz et al.
(Continued)

FOREIGN PATENT DOCUMENTS

DE      10337739     3/2005
EP      1719538 B1   9/2015
(Continued)

OTHER PUBLICATIONS

International Preliminary Report on Patentability for International Application No. PCT/EP2018/064233, dated Dec. 12, 2019.
(Continued)

*Primary Examiner* — Jennifer Dieterle
*Assistant Examiner* — Rebecca Lynee Zimmerman
(74) *Attorney, Agent, or Firm* — Jason H. Vick; Sheridan Ross, PC

(57) ABSTRACT

The present invention relates to a stent graft for implantation in vessels of a patient, wherein the stent graft has a hollow cylindrical main body made of a first prosthesis material, with a proximal end and a distal end, with a longitudinal axis c and a circumference u, at least one pocket element which is made of a second prosthesis material and which is mounted circumferentially on the outer face and/or inner face of the main body in order to form a circumferential closed pocket on a longitudinal portion of the main body, and at least one stent element which extends in a meandering formation around the main body and is received inside the pocket element.

17 Claims, 3 Drawing Sheets

(51) Int. Cl.
*A61F 2/90* (2013.01)
*A61F 2/30* (2006.01)

(52) U.S. Cl.
CPC ... *A61F 2002/075* (2013.01); *A61F 2002/077* (2013.01); *A61F 2002/30092* (2013.01); *A61F 2210/0014* (2013.01); *A61F 2230/0069* (2013.01)

(58) Field of Classification Search
CPC .... A61F 2002/30092; A61F 2210/0014; A61F 2230/0069; A61F 2/89; A61F 2002/061; A61F 2002/072; A61F 2250/0098
See application file for complete search history.

(56) References Cited

U.S. PATENT DOCUMENTS

| | | | |
|---|---|---|---|
| 6,063,112 A | 5/2000 | Sgro | |
| 2006/0036311 A1* | 2/2006 | Nakayama | A61L 31/16 623/1.15 |
| 2006/0195177 A1 | 8/2006 | Kaufmann et al. | |
| 2007/0219622 A1* | 9/2007 | Kuppurathanam | A61F 2/07 623/1.13 |
| 2012/0290068 A1* | 11/2012 | Roeder | A61F 2/07 623/1.13 |
| 2013/0102839 A1* | 4/2013 | Banas | A61F 2/82 600/36 |
| 2015/0196383 A1* | 7/2015 | Johnson | A61F 2/04 623/1.13 |

FOREIGN PATENT DOCUMENTS

| | | |
|---|---|---|
| WO | WO 97/24080 | 7/1997 |
| WO | WO 2015/126768 | 8/2015 |
| WO | WO 2016/183128 | 11/2016 |

OTHER PUBLICATIONS

International Search Report for International Application No. PCT/EP2018/064233, dated Aug. 17, 2018.
Written Opinion for International Application No. PCT/EP2018/064233, dated Aug. 17, 2018.

* cited by examiner

STENT GRAFT WITH POCKETS

CROSS REFERENCE TO RELATED APPLICATIONS

This application is a continuation of international patent application PCT/EP2018/064233, filed May 30, 2018, designating the U.S., which international patent application has been published in German language and claims priority from German patent application DE 10 2017 111 964.7, filed May 31, 2017. The entire contents of these priority applications are incorporated herein by reference.

BACKGROUND

The present invention relates to a stent graft for implantation in vessels of a patient, with a hollow-cylindrical body made of a prosthesis material, and with at least one stent element circumferentially extending the body.

Stent grafts of this type are well known in the prior art, for example from DE 103 37 739. These stent grafts are vascular prostheses, also referred to as endovascular stents/stent grafts, which are generally used to support unstable, brittle or thrombotic vessel walls and in particular to treat vessels affected by aneurysms. For this purpose, a stent graft is released at the diseased or damaged site of the vessel and restores the functionality of the original vessel or supports the still existing integrity of the vessel.

An aneurysm is understood here as a widening or bulging of an arterial blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding. The cause of a thoracic and thoraco-abdominal aortic aneurysm may be arteriosclerosis, high blood pressure and inflammation processes of the vessel wall. Injuries of the thorax due to serious accidents may also lead to an acute or chronic aortic aneurysm.

A wide variety of stent grafts are used depending on the type of application. Here, a distinction is made between balloon-expandable and self-expanding systems. The self-expandable properties result from the use of self-expanding materials such as nitinol. Balloon-expandable systems are expanded by a radial force exerted from the inside, for example when they are mounted on a balloon.

The present application is concerned with the use of so-called self-expanding stent grafts or "covered" stents.

For the treatment of aneurysms or of vessels threatening to occlude, it is already known to stabilize the affected blood vessels by implantation of a stent/stent graft in order to avoid rupture of the vessel or generally to keep the vessel open. The self-expanding stent grafts used generally consist of a hollow-cylindrical metal frame or framework, of which the lateral surface is covered by a textile or polymer film, such that a hollow-cylindrical body is obtained. The biocompatibility of the materials used has the effect that the contact between the expanded stent graft and the vessel wall is free of complications.

Another function of the textile or polymer film is to prevent the passage of blood or of blood components or deposits through the wall of the stent graft and to prevent inward growth of tissue through the wall into the interior of the stent graft. This relieves the stress on the vessel wall at the implantation site of the stent graft and prevents possible embolisms at these sites.

The metal frame of such stent grafts generally consists, for example, of a wire mesh or of so-called stent springs, which are arranged one behind the other, extend in a circumferentially meandering formation and, if appropriate, are connected to one another by connecting struts made of wire, or which are merely connected to one another via the prosthesis material. The wire mesh or the stent springs are usually made of a shape-memory material, generally of nitinol, as a result of which, after insertion into a vessel for release, the stent springs return to the expanded state and the stent graft thus "opens up".

During the implantation of the stent, the latter is radially compressed such that its cross-sectional area decreases considerably. In order to produce the compressed state, the stent graft is introduced into a sleeve, also referred to as a sleeve catheter. For this purpose, the sleeve catheter has a circumference which is smaller than the circumference of the stent graft in the expanded state. Wth the aid of an insertion system, the stent graft is brought in the compressed state to the region of the site or aneurysm that is to be treated, where it is released, wherein the position of the stent graft can be monitored via X-ray markers. After the desired position or orientation of the stent graft is obtained, the sleeve catheter is pulled back, as a result of which the stent graft is released and can expand. By virtue of the resilience of the metal frame/framework, the stent graft expands again to its original shape and in so doing stretches its lateral surface, which lodges inside the blood vessel proximally and distally in relation to the aneurysm or to the site that is to be kept open. As a result of the pressure force between the stent graft and the vessel wall, the stent graft remains fixed in position at the desired location. In this way, the blood now flows through the stent graft, preventing further stressing of the bulge and ensuring the patency of the vessel.

When positioning the stent grafts, the lateral blood vessels branching off from the main vessel must not be cut off from the blood supply by the blood-tight prosthesis material. Therefore, many stent grafts have open zones or so-called fenestrations in the jacket material or prosthesis material, through which side branches, issuing from the stent graft and projecting into the lateral vessels, can be introduced and fixed on the stent graft. This also ensures a blood supply to the body regions that are supplied by the lateral vessels.

Due to the fact that the conditions are dependent both on the vessels to be treated and on the particular patient, it is entirely reasonable to produce stent grafts that are tailor-made with respect to the anatomy of the particular vessel. However, not only is this complicated in terms of the individual design as regards length and width, the actual production of the stents is also very complicated, expensive and labor-intensive, since in some cases only one specific prosthesis can be made.

In the production of stent grafts, particularly those that have meandering stent springs and are connected to one another only via the implant material and thus indirectly, the lateral surfaces are sewn onto the metal frame/framework manually by skilled workers, which is very time-consuming and costly.

There is therefore still a great need for stent/stent graft systems, or vascular prostheses, which permit versatile use in order to satisfy the different requirements, particularly as regards the individual configuration, of the respective vessels of different patients.

The object of the present invention is therefore to make available an alternative stent graft with which the above-described disadvantages of the stent grafts known in the prior art can be overcome, and with which the production is less time-consuming and less costly.

SUMMARY

According to an embodiment, a stent graft for implantation in vessels, in particular blood vessels, of a patient, is provided wherein the stent graft has the following: a hollow-cylindrical body made of a first prosthesis material, with a proximal end and a distal end, and with a longitudinal axis c and a circumference u, at least one pocket element, which is made of a second prosthesis material and which is mounted circumferentially on the outer face and/or inner face of the body in order to form a circumferential closed pocket on a longitudinal portion of the body, and at least one stent element, which extends in a meandering formation around the body and is received inside the pocket element.

With the stent graft according to the invention, a vascular prosthesis is made available which can be used to support unstable, brittle or thrombotic vessel walls and in particular to treat vessels affected by aneurysms. This is achieved by the special configuration of the stent graft, which has a hollow-cylindrical body, made of a first prosthesis material, and also stent elements, wherein the stent elements are not fixed directly, e.g. via seams, to the body, and instead they are present in closed pocket elements provided on the outside or inside of the body and are thus in practice "free" in these pockets, i.e. not fixed by seams. The stent elements are thus mounted on the body only "indirectly" (=not fixed by seams) by being received in the pocket elements.

According to a preferred embodiment, the stent graft according to the invention is a self-expanding stent graft.

The stent graft according to the invention has the advantage that, through the provision of pocket elements and the simple reception of the stent elements inside the pocket elements, the individual stent elements do not have to be laboriously and individually fixed to the body with a large number of seams. As a result, production is greatly simplified, while the basic technical function of the stent graft or of the stent elements is maintained. Thus, production is less time-consuming and less costly. By virtue of the special configuration of the stent graft according to the invention, it is possible, for example, for manual sewing of the stent elements to be replaced by machine-made seams which form the pockets in which the stent elements are located. According to an alternative embodiment, the pockets can also be adhesively bonded or welded in the prosthesis material.

The pocket elements in which the stent elements are located can be mounted both on the inside and the outside with respect to the hollow-cylindrical body. This means that the body forms an outer jacket if the pocket elements are on the inside. In the opposite case, the body forms an inner jacket if the pocket elements are on the outside. In a further embodiment, it may be advantageous to attach the pocket elements both on the inside and on the outside.

The simple production of the stent graft according to the invention makes it possible not only to produce individual stent grafts adapted to individual patients to be treated, but also to prefabricate stent grafts that can be used universally.

According to the invention, the stent elements not only serve to give the necessary structure to the stent graft, but also to press the stent graft onto the vessel wall in the implanted state and thus to keep the stent graft in position in the vessel. The properties of the stent elements used depend on the vessel that is to be treated. For example, in the case of a vessel with a very thin wall, it is advantageous to use stent grafts that have less stiff and, in total, fewer stent elements.

The special configuration of the stent graft according to the invention moreover affords the advantage that, both on the outside and the inside, only the prosthesis material is present, which is preferably biocompatible.

By virtue of the fact that the stent elements are received in closed pocket elements, it is also possible to avoid mechanical injury or irritation of the vessel walls, which would otherwise be caused by exposed stent elements.

In the present case, "body" signifies the main body of the hollow-cylindrical stent graft, which is made of a first prosthesis material.

According to one embodiment, the at least one pocket element is shorter than the body and has a proximal end and a distal end and, lying between these, a main portion, wherein the at least one pocket element for forming the closed pocket is circumferentially secured only via its respective distal and proximal end to the outside and/or inside of the body, and the main portion is not secured to the body.

According to the invention, there is at least one pocket element on the body whose length is preferably adapted to the dimensions of the stent element respectively to be introduced.

According to one embodiment, between 1 and 30 pocket elements are provided, which are fixed at a distance from each other and separate from each other on the body.

Preferably, the stent graft according to the invention has between 3 and 25 pocket elements, more preferably between 5 and 20. Thus, 1, 2, 3, 4, 5, 6, 7, 8, 9, 10, 11, 12, 13, 14, 15, 16, 17, 18, 19, 20, 25 or 30 pocket elements are provided for the corresponding number of stent elements, which are distributed over the longitudinal axis of the body and mounted at a distance from each other. The length of the pocket elements, relative to the longitudinal axis, is always shorter than the length of the body and adapted to the dimensions of the stent elements.

It is also conceivable to provide pocket elements of different lengths, which receive different stent elements.

In the portion(s) on which the pocket elements are located, the structure is composed of two layers of prosthesis material lying one on top of the other, wherein one layer is the prosthesis material of the body and the other layer is the prosthesis material of the pocket element. The pocket element is secured circumferentially at its distal and proximal ends to the body.

A "meandering formation" is understood here to mean any loop-shaped course of a stent element.

In principle, in the case of stent grafts, the respective ends are generally referred to by the terms "distal" and "proximal", where the term "distal" designates that part or end lying farther downstream in relation to the blood flow. By contrast, the term "proximal" designates, again in relation to the blood flow, a part or the end lying farther upstream in relation to the blood flow. To put it another way, the term "distal" means in the direction of the blood flow, and the term "proximal" means counter to the direction of the blood flow. In the case of catheters, by contrast, or insertion systems, the term "distal" designates the end of the catheter or insertion system that is inserted into the patient, or the end farthest away from the user, and the term "proximal" designates the end nearer the user.

According to the invention, the division of the body of the self-expanding stent graft into proximal end portion and distal end portion signifies that the respective portions can differ in terms of having a different construction.

For example, there can be a different number of stent elements and thus also pocket elements in the portions of the body. In other words, in one embodiment, provision can be made that, in the case of a plurality of pocket elements and stent elements, these, i.e. the pocket elements, are not distributed uniformly over the longitudinal axis of the body. The stent elements received in the pocket elements can also have different diameters, which can lead to different diameters of the body.

In the present case, "stent" or "stent element" denotes any structure which gives a vascular prosthesis an expansion force and/or a supporting function. Accordingly, a stent element is therefore any element that has the properties of a stent.

The term "stent graft" is intended here, as also in the prior art, to mean a vascular prosthesis which has one or more stent elements (or stent springs) and also a prosthesis ("graft") material indirectly or directly connected thereto for forming a lumen through at least one portion of the stent graft. Such a stent graft is also referred to as a covered stent.

According to one embodiment, the pocket elements, or their ends fixed to the body, are not connected to each other directly.

According to another embodiment, the ends of the pocket elements are provided bearing directly on the ends of a successive proximal or distal pocket element.

Depending on the field of application, it is advantageous if the stent graft according to the invention has a plurality of pocket elements and stent elements present in the latter. The number of stent elements is dictated, inter alia, by the length of the required stent graft. Since the length of the stent graft is preferably between 5 and 300 cm, more preferably between 8 and 26 cm, a preferred number of prosthesis material elements is from 1 to 30, preferably between 2 and 15.

Through the number of pocket elements, the stent graft is given the desired structure and the desired properties. The presence of a plurality of closely spaced stent elements results, for example, in a less flexible vascular prosthesis, compared to one with fewer stent elements.

For the treatment of particularly thin-walled or delicate vessels, it may be advantageous if there is a continuous change in density of the stent elements within the stent graft. Thus, it may be advantageous that a particularly large number of stent elements are present in the proximal region of the stent graft, whereas the number of the stent elements decreases in the distal direction. In this way, an increasing softness of the stent graft is achieved from the proximal end to the distal end or, conversely, a continuous increase in the stiffness of the stent graft from the distal end to the proximal end.

In addition to the stent elements, it is preferred that the diameter is also adapted to the respective vessel that is to be treated. Thus, according to the invention, the stent graft, or the body of the stent graft, can have a uniform diameter over the entire length or else can have different diameters. The diameter of the stent graft is determined by the stent elements and the hollow-cylindrical body.

According to one embodiment of the stent graft according to the invention, the pocket elements are fixed to the body at a distance x of 1 mm to 30 mm, preferably between 2 mm and 15 mm.

Through the variability of the distance x from 1 mm to 30 mm, preferably between 2 mm and 15 mm, the stent graft can advantageously be adapted to the respective field of application and thus to the corresponding vessel. Thus, with a very wide spacing of the pocket elements, it is possible to obtain a stent graft that is more flexible than a stent graft in which the pocket elements are mounted at a smaller spacing.

In a development of the stent graft according to the invention, the stent element has or consists of a one-piece stent spring, with pointed arches facing alternately to the proximal and distal end of the body and parallel to the longitudinal axis c of the latter, wherein a pointed arch is formed in each case from a vertex and two legs, wherein the legs have different or identical lengths.

In the present case, a "stent spring" is understood to mean any one-piece, annular element that can be compressed on account of its material and can expand again like a spring after removal of the compression pressure. The stent springs have an undulating profile, wherein wave peak and wave valley form a phase and alternate with each other.

The stent elements or stent springs can have the same or different circumferential amplitudes, which result from the legs of the stent springs having identical lengths or different lengths. Amplitudes of different length afford the advantage that the stent graft can be adapted to the respective vessels and to the respective circumstances (curvatures, branch vessels, constrictions, etc.).

According to the invention, the stent elements can also comprise braided, twisted or laser-cut stent elements instead of the individual stent springs.

According to the invention, the stent element is enclosed within the pocket elements and is movable, i.e. not directly fixed to the first prosthesis material by seams or otherwise.

According to a further embodiment of the stent graft according to the invention, an individual stent element is received inside a pocket element.

By virtue of the design of the stent graft according to the invention, the pocket elements are made such that the freedom of movement of the stent elements within the pocket elements is greatly limited by the size of the pocket elements and by the resulting tensioning of the prosthesis material forming them, preferably to the extent of immobility of the stent elements. Thus, the stent elements can be advantageously inserted in the pocket elements in such a way that curvature of the stent graft does not cause undesired kinking or any beads of prosthesis material or accumulation of material.

Depending on the field of application, and according to another embodiment, it is also possible for individual stent elements to be located on the body not fixed in pockets, but additionally on the body, for example fixed on the inside or outside via a seam. It will be clear to a person skilled in the art that the construction of the stent graft is based on the conditions of the respective vessels which are intended to be treated with the stent graft according to the invention.

In particular, it is preferable if, in each case at the distal and/or proximal end of the body, a stent element is present which is secured directly to the first prosthesis material of the body, for example via seams.

According to a further embodiment, a stent element mounted at the proximal end of the stent graft is secured to the first prosthesis material only via its distally facing pointed arches, not its proximally facing pointing arches. According to a further embodiment, a stent element mounted at the distal end of the stent graft is secured to the first prosthesis material only via its proximally facing pointed arches.

In a preferred embodiment of the stent graft, the pocket element is sewn onto the hollow-cylindrical body. For example by a circumferential seam.

According to the invention, the circumferential seam limits the pocket in which the stent elements are located. The seam is preferably such that the stent elements can be inserted into the shaped pockets. Advantageously, the circumferential seam can be produced for example by machine, such that a saving in time and an associated saving in cost are achieved in the production of the stent graft. To produce the pockets, one end of the pocket element is first of all circumferentially sewn onto or otherwise fixed to the body. The stent element is then introduced into the still open pocket, and the pocket element is closed by sewing or otherwise fixing the second end of the pocket element.

Surgical thread is preferably used as the sewing material. This surgical thread is preferably made of polyester, polyurethane, polystyrene, polytetrafluoroethylene, ultra-high molecular weight polyethylene (UHMPE), or mixtures thereof.

In addition to fixing the pocket element to the base bodies by a seam, it is also possible according to the invention to secure it by adhesive bonding, melting or welding.

In a further preferred embodiment of the stent graft, the at least one pocket element and the stent element have substantially the same height relative to the longitudinal axis c.

Here, and overall in the present text, "substantially" means that the pocket element and the stent element do not have exactly the same height, but that an approximately identical height is also possible. This embodiment has the advantage that the stent element is more or less unable to move in the pocket on account of the defined pocket height. The pocket thus fixes the stent element by virtue of the dimensions of said pocket.

In a preferred embodiment of the stent graft, the latter has at least one side branch branching off inwardly or outwardly from the hollow-cylindrical body and extending in the distal direction parallel to the longitudinal axis of the hollow-cylindrical body.

Here, "at least one side branch branching off" signifies preferably one, two, three or four side branches.

With the side branch, the lateral surface of the body has one or at least one opening, whereby the supply to the outgoing lateral vessels is reliably ensured via the side branches of the vascular prosthesis. This is necessary when using the stent graft in vessels that have lateral vessels. It will be clear to a person skilled in the art that this depends on the conditions of the respective vessels that are to be treated with the stent graft according to the invention.

This embodiment therefore has the advantage that it can be adapted to the respective anatomical conditions of the patient who is to be treated.

In a preferred embodiment of the stent graft, a marker is located on the stent graft, which marker contains a radiopaque material or is made entirely of radiopaque material.

With the aid of the markers, which are located at specific sites of the stent graft, it is possible to precisely determine the position of the stent graft during and after the implantation and to do so very quickly.

Preferably, the radiopaque markers are made of one or more of the following materials, e.g. gold, palladium, tantalum, chromium, silver, etc. The shape of the markers can be of any kind, for example round, polygonal, and/or for example can have the shape of letters, numbers or figures that are helpful for the orientation of the stent graft in the vessel.

In a further preferred embodiment of the stent graft, the at least one stent element comprises or is formed from nitinol and can be converted from a non-expanded state to a self-expanded state.

Through the use of the self-expanding material nitinol, the stent elements have shape-memory properties.

In a preferred embodiment of the stent graft, the first and/or the second prosthesis material comprises a material that is chosen from a textile or a polymer.

In particular, it is preferable if the first and/or second prosthesis material comprises or is formed from a material chosen from polyester, polyurethane, polystyrene, polytetrafluoroethylene, ultra-high molecular weight polyethylene (UHMPE), or mixtures thereof.

In a further preferred embodiment, the first and second prosthesis materials are the same material or at least partially different materials.

According to a further embodiment, the stent graft according to the invention is to be used, as mentioned above, for the treatment of dissections or aneurysms of the blood vessels.

Furthermore, the present invention also relates to a method for releasing the stent graft according to the invention.

Further advantages will become clear from the figures and from the following description of preferred illustrative embodiments.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and shown in the drawing, in which.

EMBODIMENTS

Figure 1:
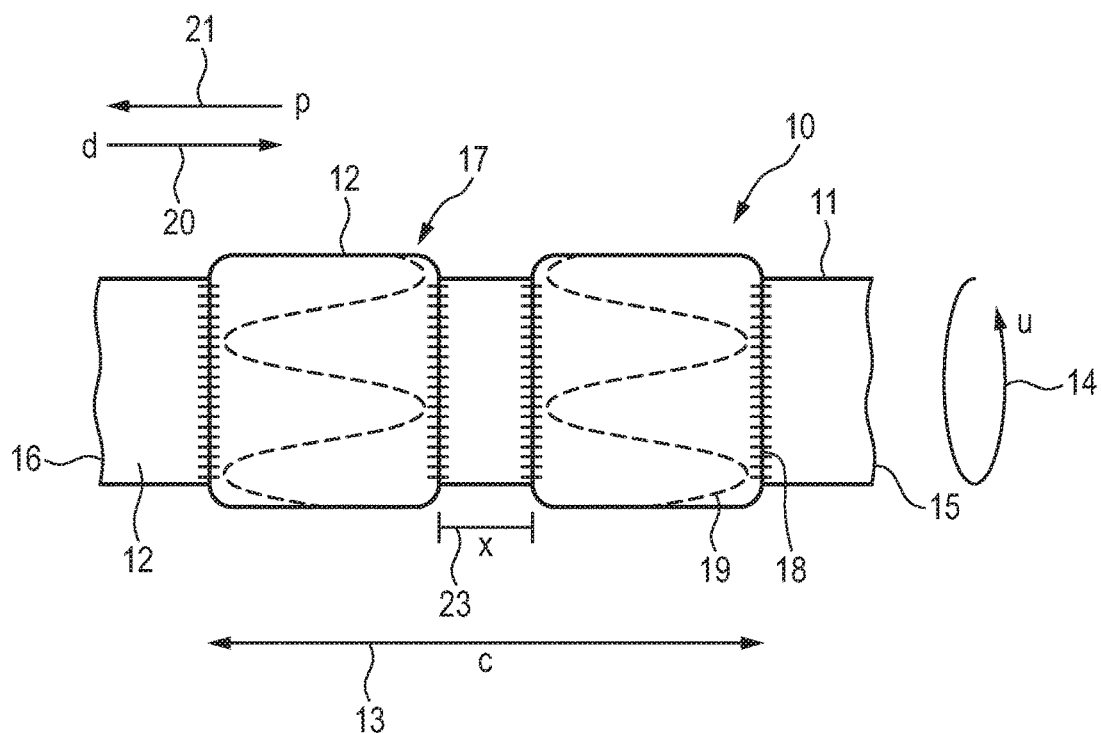
FIG. 1 shows a schematic view of an embodiment of a stent graft according to the invention in the non-inserted, expanded state, specifically a perspective view of the long side from above.
Figure 2:
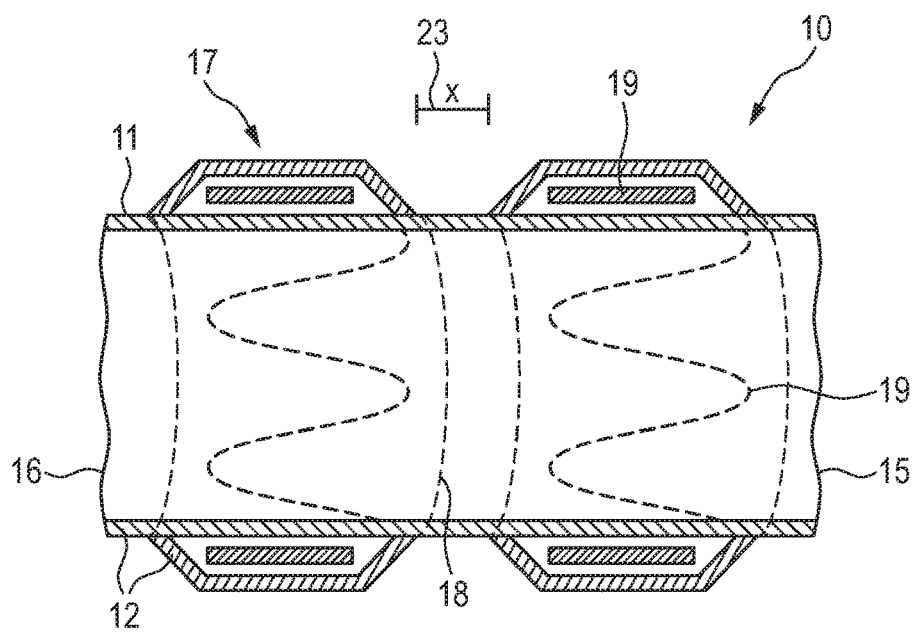
FIG. 2 shows a detail of the embodiment from FIG. 1, specifically showing a cross section along the longitudinal axis c from above.

In the figures, identical features are provided with identical reference signs. For the sake of clarity, the figures do not always show all of the reference signs.

As can be seen from FIGS. 1 to 5, the self-expanding stent graft 10 comprises a hollow-cylindrical body 11 of a first prosthesis material (graft) 12 having a longitudinal axis c 13 and a circumference u 14. The stent graft 10 also has a distal opening 15 and proximal opening 16. The body 11 forms by its construction a jacket on which hollow-cylindrical pocket elements 17 of a second prosthesis material 12 are attached by seams 18. In this case, a closed pocket 17 is formed in which the stent elements 19 are received. The stent elements 19 are preferably stent springs. In addition to the stent springs, braided, twisted or laser-cut stent elements 19 can also be used as stent elements 19 (not shown), provided that they have self-expanding properties.

The structure or the nature of the stent graft 10 is largely determined by the structure of the body 11 and also by the circumferential stent elements 19. While the body 11 defines the size or spatial dimensions, the stent elements 19 determine the self-expanding properties and also the nature (e.g. the flexibility) of the stent graft 10.

In FIGS. 1 and 3 to 5, the distal direction 20 is indicated by the arrow "d" and the proximal direction 21 by the arrow "p". In FIG. 1, the longitudinal axis 13, indicated by a double arrow, is designated by the letter "c." The circumference 14, which relates to the body 11, is provided with the letter "u".

As can be seen in all the figures, the pocket elements 17 are preferably secured to the body 11 by seams 18. In a manner not shown, they can also be secured by adhesive bonding, melting, etc.

The pocket elements 17 of the second prosthesis material 12 are configured such that the stent elements 19 fit optimally in the cavity of said pocket elements, such that they are fixed inside the pockets 17 due to the tensioning of the prosthesis material 12 and are thus more or less unable to move.

As can be seen in FIGS. 1 to 5, the body 11 forms an inner jacket. In an alternative embodiment (not shown), the body 11 can also form an outer jacket, in the interior of which the pocket-forming pocket elements 17 are secured. In a further alternative embodiment (not shown), the pockets 17 can be located on the inside and on the outside with respect to the body 11.

The stent elements 19 are preferably stent springs which extend in a meandering formation around the body 11. As can be seen from FIGS. 3 to 5, the stent springs are not necessarily identical in their size and shape.

According to the invention, the stent springs are present inside the pockets 17. Alternatively or additionally, individual stent springs can also be secured directly on the inside or outside of the body 11, preferably by means of a seam 18, as can also be seen from FIG. 5.

The stent graft 10 has substantially a constant diameter along the longitudinal axis 13. However, this depends on the particular blood vessel which is to be treated and in which the stent graft 10 is to be implanted. As can be seen in particular from FIG. 3, the proximal end 16 can have a larger circumference 14 compared to the distal end 15. This results in a continuous tapering in the distal direction 20. The different circumference 14 resulting along the longitudinal axis 13 is achieved, on the one hand, by the body 11 as such, and also by the surrounding stent springs. Thus, the stent springs in the proximal direction 21 have a greater diameter than those in the distal direction 20. A continuous change of the circumference 14 preferably results from the stent springs and also from the body 11. Here, accumulation of material, and beads of prosthetic material, are to be avoided or prevented.

Figure 3:
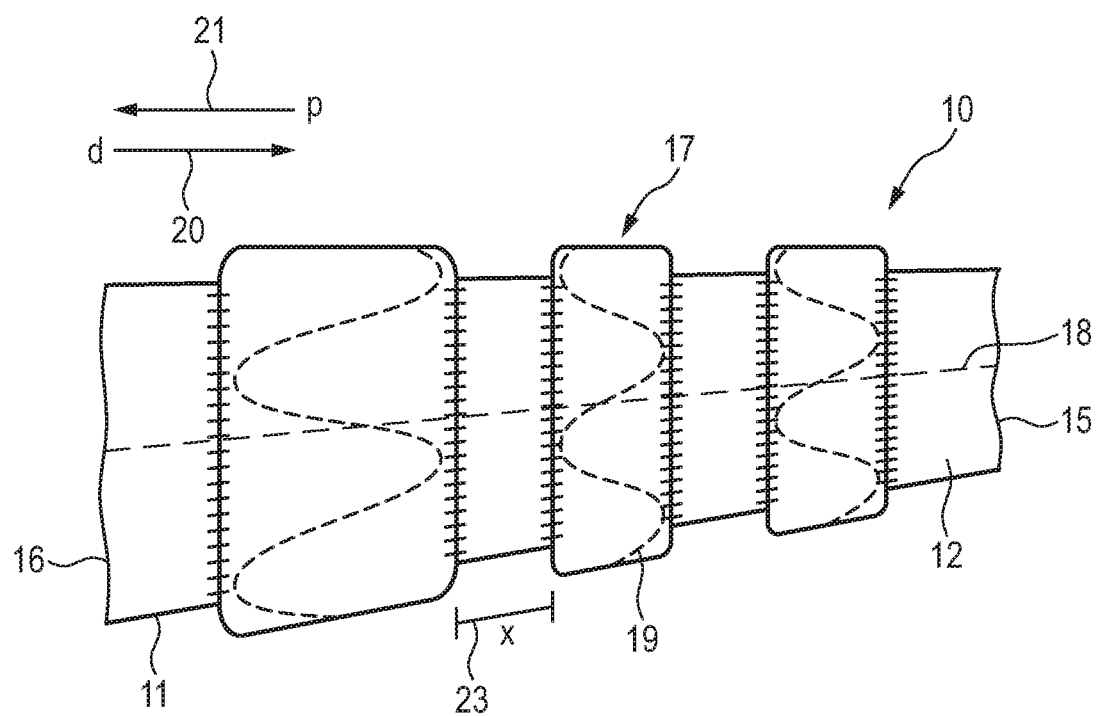
FIG. 3 shows another schematic view of a detail of the embodiment of a stent graft according to the invention, specifically a full lateral view of the long side, seen in a perspective view of the long side from above.

FIG. 3 shows that the body 11 acquires its hollow cylindrical shape by means of a seam 18 along the longitudinal axis c 13. A seam 18 is not absolutely necessary and, alternatively, the body 11 can already consist of a hollow-cylindrical prosthesis material 12.

Figure 4:
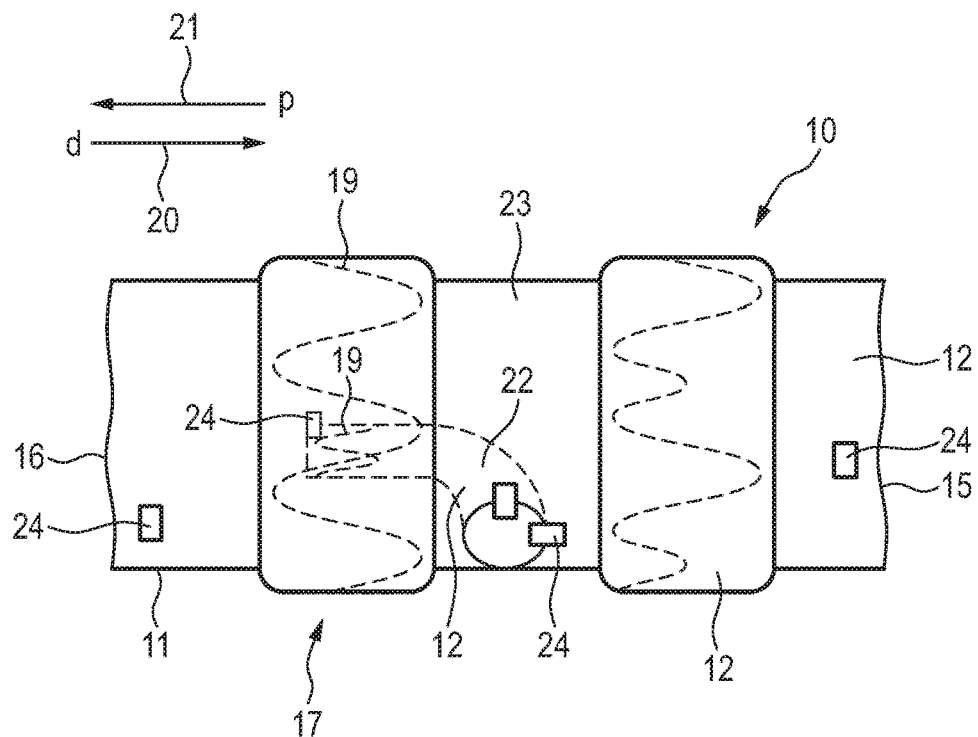
FIG. 4 shows a schematic view of a detail of the embodiment of a stent graft according to the invention which is provided with a side branch, seen in a perspective view from above.

It will also be seen from FIG. 4 that the stent graft 10 comprises a side branch 22. The latter is arranged such that it extends inwardly into the interior, i.e. into the lumen of the body 11. Thus, the side branch 22 has a first opening, which is fixedly arranged in the prosthesis material 12 of the body 11 (within the main portion x 23), and a second opening, which extends into the lumen of the body 11.

The side branch 22 has a stent element 19 located in the region of the second opening, as a result of which this opening is kept open. The stent element 19 together with the prosthesis material 12 forms the side branch 22. The side branch 22 is therefore a further smaller stent graft which is fixed to the actual stent graft 10.

The stent element, which extends in a meandering formation about the side branch 22, can be secured directly to the prosthesis material 12 by seams 18 or can be located in pockets 17 of prosthesis material 12, analogous to the stent elements 19 secured around the body 11.

The size of the side branches 22 is adapted to the respective blood vessel to be treated. According to the invention, the stent graft 10 is not limited to one side branch 22. Rather, the number of side branches 22 depends on the conditions of the vessels present in the patient.

Figure 5:
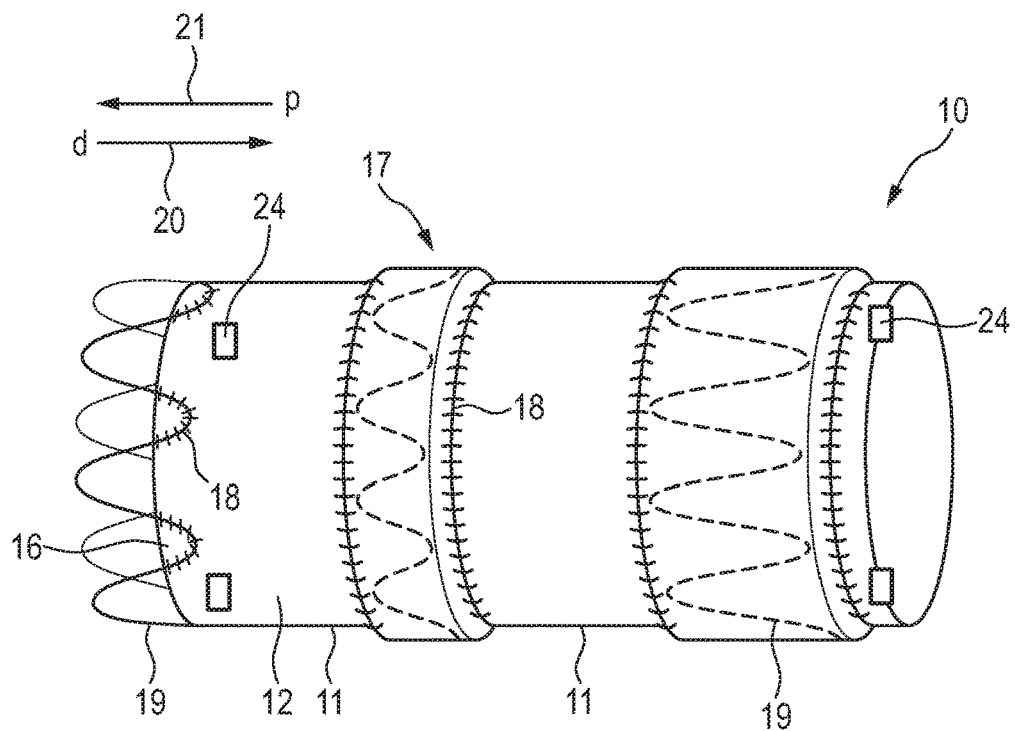
FIG. 5 shows a further schematic view of a detail of the embodiment of a stent graft according to the invention, wherein the proximal end has a partially free stent spring, seen in a perspective view of the longitudinal side laterally from above.

As can be seen from FIGS. 4 and 5, the stent graft 10 has X-ray markers 24 at specific locations. Thus, the radiopaque markers 24 are located at the distal end 15 and also around the opening of the side branch 22. The markers 24 are necessary to ensure correct positioning within the vessel during implantation. The physician performing the treatment can thus quickly and accurately determine the exact position of the stent graft 10 within the vessel by X-ray control and, if necessary, can correct it during the implantation.

On the one hand, the body 11, as shown in FIG. 1, can form the proximal and distal ends of the stent graft 10. On the other hand, one end of the stent graft 10 can also terminate with a pocket element 17 (not shown). Another possible configuration of the proximal end of the stent graft 10 is shown in FIG. 5, in which a stent spring at the proximal end 16 is only partially mounted on the body 11 of the prosthesis material 12, preferably with the aid of a seam 18.

To insert the stent graft 10 according to the invention, the stent graft 10 is loaded onto an insertion system (not shown) and held in a compressed state via a corresponding sleeve (not shown). Methods and devices for insertion of stent grafts 10 are familiar to those skilled in the art.

The stent graft 10, kept compressed, is first of all advanced into the vessel that is to be treated. The correct placement can be monitored, for example, via corresponding markers 24 provided on the stent graft 10, for example radiopaque markers 24. After correct placement, the stent graft 10 can be released by retraction of a sleeve or the like keeping the stent graft 10 compressed.

What is claimed is:

1. A stent graft configured for implantation in a vessel of a patient, wherein the stent graft includes the following:
    a hollow-cylindrical body made of a first prosthesis material, with a proximal end and a distal end, and with a longitudinal axis c and a circumference u,
    at least one pocket element, which is made of a second prosthesis material and which is mounted circumferentially on an outer and/or inner face of the body to form a circumferential closed pocket on a longitudinal portion of the body, and at least one stent element, which extends in a meandering formation around the body and is received inside the pocket element, wherein:

the at least one pocket element is shorter than the body and has a proximal end and a distal end, the body, in locations where there the at least one pocket element is not present, does not include the second prosthesis material, the at least one pocket element is circumferentially secured only via its respective distal and proximal end to the outer and/or inner face of the body, and between 1 and 30 pocket elements are provided, which are fixed at a distance from each other and are separate from each other on the body.

2. The stent graft as claimed in claim 1, wherein the pocket elements are fixed at a distance apart of 1 mm to 30 mm on the body.

3. The stent graft as claimed in claim 1, wherein the stent element includes a one-piece stent spring, with pointed arches facing alternately to the proximal and distal end of the body and parallel to the longitudinal axis c of the body, wherein a pointed arch is formed in each case from a vertex and two legs, wherein the legs have different or identical lengths.

4. The stent graft as claimed in claim 1, wherein an individual stent element is received inside a pocket element.

5. The stent graft as claimed in claim 1, wherein the pocket element is sewn onto the hollow-cylindrical body.

6. The stent graft as claimed in claim 1, wherein the pocket element and the stent element have substantially the same height, relative to the longitudinal axis c.

7. The stent graft as claimed in claim 1, wherein the stent graft has at least one side branch branching off inwardly or outwardly from the hollow-cylindrical body and extending in the distal direction parallel to the longitudinal axis of the hollow-cylindrical body.

8. The stent graft as claimed in claim 1, wherein a marker is located on the stent graft, which marker contains a radiopaque material or is made entirely of radiopaque material.

9. The stent graft as claimed in claim 1, wherein the at least one stent element comprises or is formed from nitinol and can be converted from a non-expanded state to a self-expanded state.

10. The stent graft as claimed in claim 1, wherein the first and/or second prosthesis material comprises a material that is chosen from a textile or a polymer.

11. The stent graft as claimed in claim 1, wherein the first and/or second prosthesis material comprises a material that is chosen from polyester, polyurethane, polystyrene, polytetrafluoroethylene, ultra-high molecular weight polyethylene (UHMPE), or mixtures thereof.

12. The stent graft as claimed in claim 1, wherein the first and second prosthesis materials are the same material or at least partially different materials.

13. The stent graft as claimed in claim 1, wherein the body which is located between the individual pockets is formed from only one prosthetic material.

14. The stent graft as claimed in claim 1, wherein the second prosthesis material ends at the proximal end and the distal end of the at least one pocket element.

15. A stent graft comprising:

a hollow-cylindrical body made of a first prosthesis material, the body having a proximal end and a distal end, and with a longitudinal axis and a circumference;

at least one pocket, located between the proximal end and the distal end of the body, made of a second prosthesis material, the at least one pocket mounted circumferentially on an outer and/or an inner face of the body and forming a circumferential closed pocket on a longitudinal portion of the body, and at least one stent element, which extends in a formation around the body and is received inside the pocket element, wherein:

the at least one pocket is shorter than the body and has a proximal end and a distal end, the body, in locations where there the at least one pocket element is not present, does not include the second prosthesis material, the at least one pocket is circumferentially secured only via its respective distal and proximal end to the outer and/or an inner face of the body, and between 1 and 30 pockets are provided which are fixed at a distance from each other and are separated from each other along the body.

16. The stent graft as claimed in claim 1, wherein a first side of the at least one stent element is immediately adjacent to the outside and/or inside face of the body.

17. The stent graft as claimed in claim 1, wherein a first side of the at least one stent element is immediately adjacent to the outer and/or inner face of the body.

* * * * *

UNITED STATES PATENT AND TRADEMARK OFFICE
CERTIFICATE OF CORRECTION

PATENT NO. : 11,484,399 B2
APPLICATION NO. : 16/693850
DATED : November 1, 2022
INVENTOR(S) : Stefan Derkvist It is certified that error appears in the above-identified patent and that said Letters Patent is hereby corrected as shown below:

On the Title Page

Item (63) "Related U.S. Application Data", Column 1, Line 16, please delete "PCT/EP2018/065233" and insert -- PCT/EP2018/064233 --, therefore.

Signed and Sealed this
Thirteenth Day of February, 2024

Katherine Kelly Vidal
Director of the United States Patent and Trademark Office